United States Patent
Osborne

(10) Patent No.: US 11,512,346 B2
(45) Date of Patent: Nov. 29, 2022

(54) METHOD FOR SEQUENCING A DIRECT REPEAT

(71) Applicant: GENOME RESEARCH LIMITED, Cambridge (GB)

(72) Inventor: Robert Osborne, Great Chesterford (GB)

(73) Assignee: GENOME RESEARCH LIMITED, Cambridge (GB)

( * ) Notice: Subject to any disclaimer, the term of this patent is extended or adjusted under 35 U.S.C. 154(b) by 0 days.

(21) Appl. No.: 17/435,687

(22) PCT Filed: Feb. 27, 2020

(86) PCT No.: PCT/IB2020/051702
§ 371 (c)(1),
(2) Date: Sep. 1, 2021

(87) PCT Pub. No.: WO2020/183280
PCT Pub. Date: Sep. 17, 2020

(65) Prior Publication Data
US 2022/0042092 A1    Feb. 10, 2022

Related U.S. Application Data

(60) Provisional application No. 62/818,527, filed on Mar. 14, 2019.

(51) Int. Cl.
*C12Q 1/6869*      (2018.01)
(52) U.S. Cl.
CPC .................................. *C12Q 1/6869* (2013.01)
(58) Field of Classification Search
None
See application file for complete search history.

(56) References Cited

U.S. PATENT DOCUMENTS

2008/0009420 A1*   1/2008   Schroth ................ C12Q 1/6848
                                                         506/16
2016/0304954 A1*   10/2016   Lin ...................... C12Q 1/6874
2020/0199584 A1    6/2020   Osborne et al.

FOREIGN PATENT DOCUMENTS

WO        2018/229547 A1    12/2018

OTHER PUBLICATIONS

Eyre et al., "Comparison of Multilocus Variable-Number Tandem-Repeat Analysis and Whole-Genome Sequencing for Investigation of Clostridium difficile Transmission", Journal of Clinical Microbiology, Dec. 2013, 51(12): 4141-4149.

* cited by examiner

*Primary Examiner* — Nianxiang Zou
(74) *Attorney, Agent, or Firm* — James S. Keddie; Bozicevic, Field & Francis LLP

(57) ABSTRACT

Described herein is a method of sequencing a template that comprises a direct repeat, comprising: (a) in the same reaction, hybridizing a primer to a first site that is upstream of the first repeat sequence and hybridizing a primer to a second site that is upstream of the second repeat sequence, wherein the first and second sites are: (i) upstream of the first and second repeat sequences, respectively, and (ii) equidistant from the first and second repeat sequences; and (b) subjecting the hybridization product of (a) to a sequencing-by-synthesis sequencing reaction to produce a sequence read that comprises a combination of the first and second repeat sequences.

19 Claims, 4 Drawing Sheets

Specification includes a Sequence Listing.

METHOD FOR SEQUENCING A DIRECT REPEAT

CROSS-REFERENCING

This application is a § 371 national phase of International Application No. PCT/IB2020/051702, filed on Feb. 27, 2020, which claims the benefit of U.S. provisional application Ser. No. 62/818,527, filed on Mar. 14, 2019, which applications are incorporated by reference herein.

BACKGROUND

Some sequencing methods require comparing two sequences with a single sequence read to determine if there is a difference between the sequences. However, such methods can be challenging to perform because the software that performs this task needs to accurately identify the beginnings and ends of the sequences in a sequence read that should be compared, extract sequences that should be compared, and then perform an alignment of those sequence. These steps can be challenging to automatically perform consistently for all different sequences, sequence compositions and lengths. For example, the existence of repeated sequences within a sequence read can cause slippage of an alignment, which may produce erroneous results.

The present disclosure provides an alternative, better way for comparing sequences with the same sequence read.

SUMMARY

A method of sequencing a template that comprises a direct repeat, i.e., template comprising a first repeat sequence and a second repeat sequence that is in direct orientation with the first repeat is provided. In some embodiments, the method may comprise, in the same reaction, hybridizing a primer to a first site that is upstream of the first repeat sequence and hybridizing a primer to a second site that is upstream of the second repeat sequence. In these embodiments the first and second sites (i.e., the sites to which the first and second primers bind) should be upstream of the first and second repeat sequences, respectively (i.e., downstream from the 3' ends of the primers) and equidistant from the first and second repeat sequences. The hybridization product produced by this step contains the template with two primers annealed to it, both upstream of a repeat sequence by the same distance (e.g., the same number of bases). Next, the method involves sequencing the template using a sequencing-by-synthesis method (e.g., using fluorescent dye terminators) to produce a sequence read that comprises a combination of the first and second repeat sequences, i.e., a sequence read that is essentially two reads (one from the first primer and the other from the second primer) that are merged with one another. Differences between the sequence of the first and second repeats can be identified as low-quality base calls.

In some embodiments, within each template molecule the first repeat sequence and the second repeat sequence are amplified from opposite strands of a double-stranded fragment of DNA. In these embodiments, the sequences of the first and second repeats should be identical except for positions that correspond to damaged nucleotides in the double-stranded fragment of DNA or errors that occur during amplification. Thus, any differences between the top and bottom strands of the double-stranded fragment can be identified in the sequence read as a "low quality" base call, i.e., a base that is associated with poor underlying data due to there being, in effect, two different bases at a particular position in the sequence. In more detail, within each template molecule the first repeat may be amplified from the one strand of a double-stranded fragment of genomic DNA and the second repeat may be amplified from the other strand of the same fragment of double-stranded fragment of genomic DNA. Within a molecule, the sequences of the first and second repeats are often the same. However, in cases where there is damage in the original molecule, the sequences of the first and second repeats (within a single molecule) may differ. As such, within each repeat molecule, the first and second repeats are typically identical except for positions that correspond to (a) damaged nucleotides in the double-stranded fragment of genomic DNA from which those strands were copied or (b) errors that occur during amplification of the direct repeat molecule (e.g., nucleotides that are mis-incorporated or deletions caused by a stutter or slippage event during amplification). As such, the first and second repeats are typically at least 95% identical in sequence. Thus, the different repeats in a template molecule can be sequenced using two primers (one for each repeat) at the same time to determine if the repeats (which correspond to the top and complement of the bottom strands of an initial fragment of genomic DNA) differ. Because two primers are used, the sequences of the first and second repeats are merged in the same sequence read. Any differences between those sequences can be observed as a low-quality base call because the underlying data for that base call are essentially derived from two bases (one base read by the first primer and the other base read by the second primer, where those bases are the same distance downstream from the primers). If there is a low-quality base call at a particular position, then the method may comprise excluding that base call from future analysis. The method may be used to identify damaged nucleotides and amplification errors, as well as sequencing errors (i.e., errors that stem from the sequence reaction itself, not in the sequencing template).

The method finds particular use in analyzing samples of DNA that contain damaged DNA, samples in which the amount of DNA is limited and/or samples that contain fragments having a low copy number mutation (e.g., a sequence caused by a mutation that is present at low copy number relative to sequences that do not contain the mutation). These features are often present in patient samples that can be obtained non-invasively, e.g., circulating tumor (ctDNA) samples, which can be obtained from peripheral blood, or invasively, e.g., tissue sections. In some embodiments, the sample may be DNA obtained from tissue embedded in paraffin (i.e., an FFPE sample). In such samples, the mutant sequences may only be present at a very limited copy number (e.g., less than 10, less than 5 copies or even 1 copy in a background of hundreds or thousands of copies of the wild type sequence). In these situations, without an effective way to eliminate errors generated by DNA damage, it can be almost impossible to identify a true sequence variation with significant confidence.

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
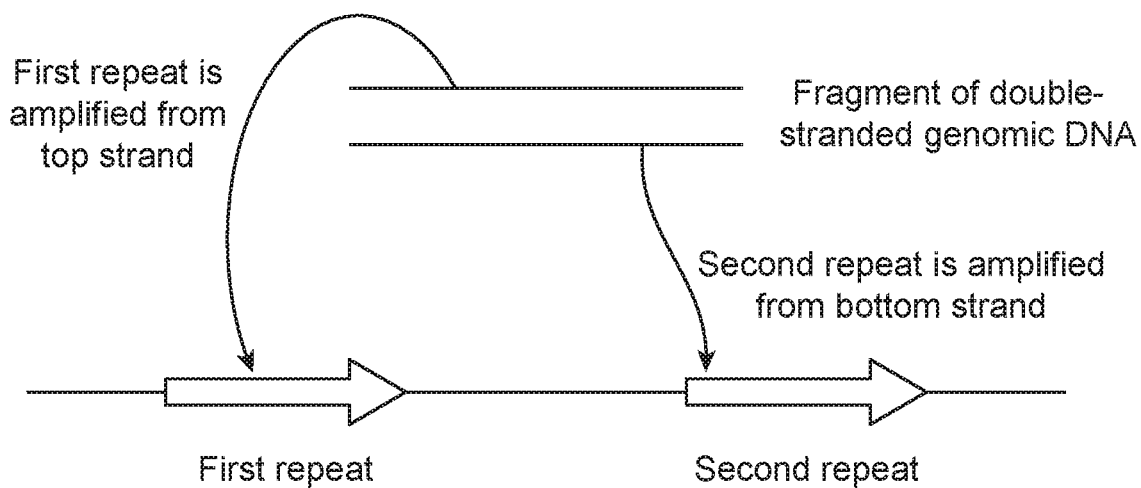
FIG. 1 schematically illustrates a direct repeat template that has been made from a fragment of double-stranded genomic DNA.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "sample" as used herein relates to a material or mixture of materials, typically containing one or more analytes of interest. In one embodiment, the term as used in its broadest sense, refers to any plant, animal, microbial or viral material containing genomic DNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acids, e.g., genomic DNA from tissue culture cells or a sample of tissue, may be employed herein.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct, and the array is addressable.

The term "nucleotide" is intended to include those moieties that can be copied using a polymerase. Nucleotides contain not only the known purine and pyrimidine bases, but also other heterocyclic bases that have been modified e.g., "damaged" bases that have oxidized or deadenylated for example. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. In some embodiments a primer can be activated prior to primer extension. For example, some primers have a 3' block and internal RNA base. The RNA base can be removed by RNaseH or another treatment, thereby producing a 3' hydroxyl group which can be extended. Other methods for activating primers exist.

Primers are usually single-stranded for maximum efficiency in amplification but may alternatively be double-stranded or partially double-stranded. If double-stranded, the primer is usually first treated to separate its strands before being used to prepare extension products. This denaturation step is typically affected by heat, but may alternatively be carried out using alkali, followed by neutralization. Also included in this definition are toehold exchange primers, as described in Zhang et al (Nature Chemistry 2012 4: 208-214), which is incorporated by reference herein.

Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of a nucleic acid strand anneals to and forms a stable duplex, either a homoduplex or a heteroduplex, under normal hybridization conditions with a second complementary nucleic acid strand and does not form a stable duplex with unrelated nucleic acid molecules under the same normal hybridization conditions. The formation of a duplex is accomplished by annealing two complementary nucleic acid strand regions in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein.

The terms "determining," "measuring," "evaluating," "assessing," "assaying," and "analyzing" are used interchangeably herein to refer to any form of measurement and include determining if an element is present or not. These terms include both quantitative and/or qualitative determinations. Assessing may be relative or absolute. "Assessing the presence of" includes determining the amount of something present, as well as determining whether it is present or absent.

The term "ligating," as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "Watson" (or "top") and "Crick" (or "bottom") strands. In certain cases, complementary strands of a chromosomal region may be referred to as "plus" and "minus" strands, the "first" and "second" strands, the "coding" and "noncoding" strands, the "top" and "bottom" strands or the "sense" and "antisense" strands. The assignment of a strand as being a Watson or Crick strand is arbitrary and does not imply any particular orientation, function or structure.

The term "extending", as used herein, refers to the extension of a primer by the addition of nucleotides using a polymerase. If a primer that is annealed to a nucleic acid is extended, the nucleic acid acts as a template for extension reaction.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "barcode sequence" or "molecular barcode", as used herein, refers to a unique sequence of nucleotides that can be used to a) identify and/or track the source of a polynucleotide in a reaction, b) count how many times an initial molecule is sequenced and c) pair sequence reads from different strands of the same molecule. Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al., Proc. Natl. Acad. Sci., 97: 1665-1670 (2000); Shoemaker et al., Nature Genetics, 14: 450-456 (1996); Morris et al., European patent publication 0799897A1; Wallace, U.S. Pat. No. 5,981,179; and the like. In particular embodiments, a barcode sequence may have a length in range of from 2 to 36 nucleotides, or from 6 to 30 nucleotides, or from 8 to 20 nucleotides.

In some cases, a barcode may contain a "degenerate base region" or "DBR", where the terms "degenerate base region" and "DBR" refers to a type of molecular barcode that has complexity that is sufficient to help one distinguish between fragments to which the DBR has been added. In some cases, substantially every tagged fragment may have a different DBR sequence. In these embodiments, a high complexity DBR may be used (e.g., one that is composed of at least 10,000 or 100,000, or more sequences). In other embodiments, some fragments may be tagged with the same DBR sequence, but those fragments can still be distinguished by the combination of i. the DBR sequence, ii. the sequence of the fragment, iii. the sequence of the ends of the fragment, and/or iv. the site of insertion of the DBR into the fragment. In some embodiments, at least 95%, e.g., at least 96%, at least 97%, at least 98%, at least 99% or at least 99.5% of the target polynucleotides become associated with a different DBR sequence. In some embodiments, a DBR may comprise one or more (e.g., at least 2, at least 3, at least 4, at least 5, or 5 to 30 or more) nucleotides selected from R, Y, S, W, K, M, B, D, H, V, N (as defined by the IUPAC code). In some cases, a double-stranded barcode can be made by making an oligonucleotide containing degenerate sequence (e.g., an oligonucleotide that has a run of 2-10 or more "Ns") and then copying the complement of the barcode onto the other strand, as described below.

Oligonucleotides that contain a variable sequence, e.g., a DBR, can be made by making a number of oligonucleotides separately, mixing the oligonucleotides together, and by amplifying them en masse. In other words, the population of oligonucleotides that contain a variable sequence can be made as a single oligonucleotide that contains degenerate positions (i.e., positions that contain more than one type of nucleotide). Alternatively, such a population of oligonucleotides can be made by fabricating them individually or using an array of the oligonucleotides using in situ synthesis methods, cleaving the oligonucleotides from the substrate and optionally amplifying them. Examples of such methods are described in, e.g., Cleary et al. (Nature Methods 2004 1: 241-248) and LeProust et al. (Nucleic Acids Research 2010 38: 2522-2540).

In some cases, a barcode may be error correcting. Descriptions of exemplary error identifying (or error correcting) sequences can be found throughout the literature (e.g., in are described in US patent application publications US2010/0323348 and US2009/0105959 both incorporated herein by reference). Error-correctable codes may be necessary for quantitating absolute numbers of molecules. Many reports in the literature use codes that were originally developed for error-correction of binary systems (Hamming codes, Reed Solomon codes etc.) or apply these to quaternary systems (e.g. quaternary Hamming codes; see Generalized DNA barcode design based on Hamming codes, Bystrykh 2012 PLoS One. 2012 7: e36852).

In some embodiments, a barcode may additionally be used to determine the number of initial target polynucleotide molecules that have been analyzed, i.e., to "count" the number of initial target polynucleotide molecules that have been analyzed. PCR amplification of molecules that have been tagged with a barcode can result in multiple sub-populations of products that are clonally-related in that each of the different sub-populations is amplified from a single tagged molecule. As would be apparent, even though there may be several thousand or millions or more of molecules in any of the clonally-related sub-populations of PCR products and the number of target molecules in those clonally-related sub-populations may vary greatly, the number of molecules tagged in the first step of the method can be estimated by counting the number of DBR sequences associated with a target sequence that is represented in the population of PCR products. This number is useful because, in certain embodiments, the population of PCR products made using this method may be sequenced to produce a plurality of sequences. The number of different barcode sequences that are associated with the sequences of a target polynucleotide can be counted, and this number can be used (along with, e.g., the sequence of the fragment, the sequence of the ends of the fragment, and/or the site of insertion of the DBR into the fragment) to estimate the number of initial template nucleic acid molecules that have been sequenced. Such tags can also be useful in correcting sequencing errors.

The terms "sample identifier sequence" or "sample index" refer to a type of barcode that can be appended to a target polynucleotide, where the sequence identifies the source of the target polynucleotide (i.e., the sample from which the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "adapter" refers to a nucleic acid that can be joined to at least one strand of a double-stranded DNA molecule. The term "adapter" refers to molecules that are at least partially double-stranded. An adaptor may be 20 to 150 bases in length, e.g., 40 to 120 bases, although adaptors outside of this range are envisioned.

The term "adaptor-tagged," as used herein, refers to a nucleic acid that has been tagged by, i.e., covalently linked with, an adaptor. An adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation.

The term "complexity" refers to the total number of different sequences in a population. For example, if a population has 4 different sequences then that population has a complexity of 4. A population may have a complexity of at least 4, at least 8, at least 16, at least 100, at least 1,000, at least 10,000 or at least 100,000 or more, depending on the desired result.

The term "of the formula" means that the individual molecules in a population are described by, i.e., encompassed by, the formula.

Certain polynucleotides described herein may be referred to by a formula. Unless otherwise indicated the polynucleotides defined by a formula are oriented in the 5' to 3' direction. The components of the formula refer to separately definable sequences of nucleotides within a polynucleotide, where, unless implicit from the context, the sequences are linked together covalently such that a polynucleotide described by a formula is a single molecule. In some cases, the components of the formula are immediately adjacent to one another in the single molecule. Unless otherwise indicated or implicit from the context, a region defined by a formula may have additional sequences, a primer binding site, a molecular barcode, a promoter, or a spacer, etc., at its 3' end, its 5' end or both the 3' and 5' ends. As would be apparent, the various component sequences of a polynucleotide may independently be of any desired length as long as they are capable of performing the desired function (e.g., hybridization to another sequence). For example, the various component sequences of a polynucleotide may independently have a length in the range of 8-80 nucleotides, e.g., 10-50 nucleotides or 12-30 nucleotides.

The term "opposite strands", as used herein, refers to the top and bottom strands, where the strands are complementary to one another, except for damaged nucleotides.

The term "potential sequence variation", as used herein, refers to a sequence variation, e.g., a substitution, deletion, insertion or rearrangement of one or more nucleotides in one sequence relative to another.

The term "amplification error" refers to a mis-incorporated base, or a deletion/insertion caused by polymerase stutter. Stutter usually occurs in repeat sequences, e.g., short tandem repeats (STRs) or microsatellite repeats and is presumed to be due to miscopying or slippage by the polymerase The term "target enrichment", as used herein, refers to a method in which selected sequences are separated from other sequences in a sample. This may be done by hybridization to a probe, e.g., hybridizing a biotinylated oligonucleotide to the sample to produce duplexes between the oligonucleotide and the target sequence, immobilizing the duplexes via the biotin group, washing the immobilized duplexes, and then releasing the target sequences from the oligonucleotides. Alternatively, a selected sequence may be enriched by amplifying that sequence, e.g., by PCR using one or more primers that hybridize to a site that is proximal to the target sequence.

The terms "minority variant" and "sequence variation", as used herein, is a variant that is present at a frequency of less than 50%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:5 or less, 1:10 or less, 1:100 or less, 1:1,000 or less, 1:10,000 or less, 1:100,000 or less or 1:1,000,000 or less.

The term "duplex sequencing" refers to a method in which sequences for both strands of a double-stranded molecule of genomic DNA are obtained. In duplex sequencing, the sequences derived from the top strand of double-stranded molecule of genomic DNA are distinguishable from sequences derived from the bottom strand of that molecule in such a way that the sequences for the top and bottom strands from the same double-stranded molecule of genomic DNA can be compared.

The term "direct repeat" refers a molecule that contains two copies of near identical sequences, i.e., sequences that are of the same length and that are at least 95% identical in nucleotide sequence.

The term "distance" as used herein depends on the sequencing-by-synthesis method being used for sequencing. For example, in methods that rely on reversible chain terminators the distance between the 3' end of a primer and a downstream nucleotide can be defined by the number of bases. In semiconductor or pyrosequencing methods the distance between the 3' end of a primer and a downstream nucleotide can be defined by the number of flows because, in those methods, several nucleotides can be added in a single flow. Thus, "equidistant" can mean the same number of nucleotides if a reversible chain terminator-based sequencing method is used or the same number of flows if a semiconductor- or pyrosequencing-based sequencing methods is used.

For ease of reference, the reverse complement of a sequence may be indicated by the prime ("'") symbol. For example, the reverse complement of a sequence referred to as "W" is may be referred to as "W'".

Other definitions of terms may appear throughout the specification.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Provided herein, among other things, is a way to sequence a template that has a direct repeat, i.e., a template that comprises a first repeat sequence and a second repeat sequence, wherein the first and second repeat sequences are in a direct repeat and either identical or nearly identical. In some embodiments within each template molecule, the first repeat sequence and the second repeat sequence may be amplified from opposite strands of a double-stranded fragment of DNA. In embodiments in which the fragment of DNA is double-stranded genomic DNA (e.g., eukaryotic genomic DNA, which may be isolated from a tissue biopsy or may be cell-free DNA (cfDNA), microbial genomic DNA or viral genomic DNA), the sequences of the repeats may be identical except for positions that correspond to damaged nucleotides in the double-stranded fragment of DNA or errors that occur during amplification. An example of such a direct repeat is illustrated in FIG. 1. As shown, within each repeat molecule the first repeat and the second repeat are amplified from opposite strands of a fragment of double-stranded genomic DNA, e.g., genomic DNA. The first repeat has the same or a very similar sequence as one strand (the top strand of the fragment, for example) of a fragment of double-stranded genomic DNA whereas the second repeat has the same or a very similar sequence as the reverse complement of the other strand of the fragment (e.g., the bottom strand of the fragment). In embodiments, in which the fragment is genomic DNA, the first and second repeat sequences should be identical except for nucleotides that correspond to (i.e., are at a position that corresponds to the position of) damaged nucleotides in the fragment of double-stranded genomic DNA or errors that have occurred during amplification. In other embodiments, the double-stranded fragment may be made synthetically or derived from a double-stranded plasmid, for example.

A "damaged nucleotide" refers to any derivative of adenine, cytosine, guanine, and thymine that has been altered in a way that allows it to pair with a different base. In non-damaged DNA, A base pairs with T and C base pairs with G. However, some bases can be oxidized, alkylated or deaminated in a way that effects base pairing. For example, 7,8-dihydro-8-oxoguanine (8-oxo-dG) is a derivative of guanine that base pairs with adenine instead of cytosine. This derivative causes a G to T transversion after replication. Deamination of cytosine produces uracil, which can base pair with adenine, leading to a C to T change after replication. Other examples or damaged nucleotide that are capable of mismatched pairing include are known.

Within a direct repeat template molecule, the sequences of first and second repeats have identical lengths and are at least 95% identical (e.g., at least 95% identical, at least 96% identical, at least 97% identical, at least 98% identical, at least 99% identical or 100% identical, depending on, e.g., the extent of DNA damage in the fragment of double-stranded genomic DNA and/or amplification errors) and, with the exception of nucleotides that correspond to damaged nucleotides and amplification errors, should be identical. As shown, the molecules may have a unit length of 1, meaning that there is only one copy of first repeat and one copy of the second repeat in each molecule. The template molecules may be single stranded or double stranded. However, as would be appreciated, the template is in its single stranded form when it is being sequenced. The sequence of the first and second repeats may have a length of at least 50 nucleotides and in some embodiments may be in the range of 50 nucleotides to 2 kb in length, e.g., 50-500 nt or 50-300 nt. In some embodiments, the direct repeat template may be in a sample that contains other direct repeat templates. Within the population, the complexity and median length of the sequence of the first repeat may vary and may be approximately the same as the complexity and median length of the sequence of the second repeat, since those sequences are almost identical. In the population, the first repeat and the second repeat may each have a complexity of at least $10^3$, e.g., at least $10^4$, at least $10^5$, at least $10^6$, at least $10^7$, at least $10^8$, at least $10^9$ or at least $10^{10}$, for example, meaning that in the population, the first repeat and the second repeat are each represented by at least $10^3$ different sequences. The lengths of the first and second repeats may depend on the lengths of the fragments of DNA in the sample from which the molecules are made. In some embodiments, the fragments may have a median size that no more than 2 kb in length (e.g., in the range of 50 bp to 2 kb, e.g., 75 bp to 1.5 kb, 100 bp to 1 kb, 100 bp to 500 bp). The lengths of the fragment may be tailored to the sequencing platform being used. Examples of how these molecules can be made will be described in greater detail below.

Therefore, in any embodiment, the direct repeat molecule may be made by copying a double-stranded fragment of DNA to produce the direct repeat molecule, where the first and second repeats of the direct repeat molecule are to be amplified from opposite strands of the double-stranded fragment of DNA.

Figure 2:
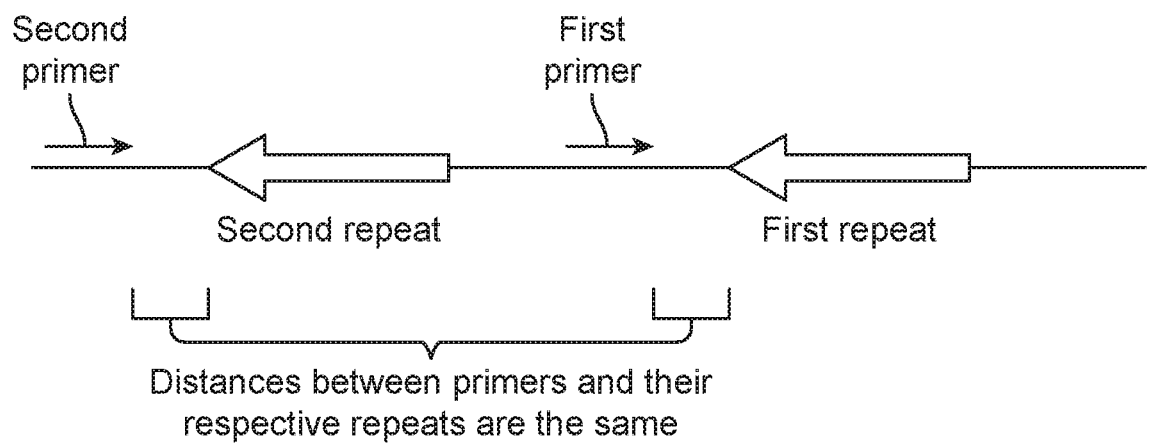
FIG. 2 schematically illustrates where the first and second primers used in the method hybridize a direct repeat template.

As noted above, in some embodiments the method may comprise, in the same reaction, hybridizing a primer to a first site that is upstream of the first repeat sequence and hybridizing a primer to a second site that is upstream of the second repeat sequence. In these embodiments, the first and second sites (i.e., the sites to which the first and second primers bind, respectively) are upstream of the first and second repeat sequences, respectively, and equidistant from the first and second repeat sequences. This is illustrated in FIG. 2. As illustrated, the first primer binds to a site that is upstream of (i.e., 3' to) the first repeat whereas the second primer binds to a site that is upstream of (i.e., 3' to) the second repeat, where the distances between the primers and their respective repeats are the same. Illustrated by example, if the 3' end of the first primer hybridizes to a nucleotide that is upstream of (i.e., 3' to) the first repeat by n bases (where n is in the range of, e.g., 5 to 30) then the 3' end of the second primer hybridizes to a nucleotide that is upstream of (i.e., 3' to) the second repeat by n bases. While the distance between the primer binding sites and the repeats can be defined by the number of bases for some sequencing methods (e.g., Illumina's dye terminator sequencing method), the distance can be defined by "flows" in other methods (e.g. Ion Torrent or pyrosequencing methods).

After hybridization of the primers, the method may comprise subjecting the hybridization product to a sequencing-by-synthesis sequencing reaction to produce a sequence read that comprises a combination of the first and second repeat sequences, meaning that the sequences are merged into one. In some embodiments, sequencing-by-synthesis methods are those that involve extending a primer using a template and detecting which nucleotide is added at each position. Sequencing-by-synthesis methods included, but are not limited to, Illumina's reversible dye terminator method, Thermo's Ion Torrent method (which detects ions as they are released by DNA polymerase) and pyrosequencing, although others are known. In the reversible dye terminator approach, the sequence of a template is determined using reversible terminators chemistry (Turcatti et al., Nucleic Acids Res. 2008 36:e25). In every sequencing cycle a single fluorescently labeled, 3'-blocked nucleotide is added in a templated primer extension reaction. After incorporation, the identity of the fluorescent label added is detected by fluorescent imaging. In each round, the labels and terminators are chemically removed in order to prepare the primer extension product the next cycle. A more detailed description of the process can be found in Bentley, supra.

As noted above, the sequence read produced using this method will be a combination of the first and the second repeat sequences, where the term "combination" is intended to mean that the sequences of the first and second repeats are merged, superimposed or melded into one. By way of example, if the sequence of the first repeat is GATCG-GATCGA (SEQ ID NO: 1) and sequence of the second repeat is GATCGGATCGA (SEQ ID NO: 1), then the sequence read will contain only one copy of the sequence GATCGGATCGA (SEQ ID NO: 1), where some of the signal used to generate the sequence read is generated by extension of the first primer and some of the signal used to generate the sequence read is generated by the extension of the second primer in the same reaction.

Differences in the sequences of the first and second repeats can be identified because the underlying signal corresponding to the difference will be mixed (i.e., will be a composite of signals produced by two different bases at that position). Positions that have a mixed signal can be identified because they are associated with a low-quality base call. As such, differences in the sequences of the first and second repeats can be identified as positions that have a low-quality base call. In these embodiments, the sequence read comprises, for each position of the sequence read, a quality score indicating the reliability of the base(s) called at that position. Base calling is the process by which an order of nucleotides in a template is inferred during a sequencing reaction. For example, next generation sequencing platforms that use fluorescently labeled reversible terminators have a unique color for each base. These are incorporated into the complementary strand of the DNA template and captured with a sensitive CCD camera. These images are processed into signals which are used to infer the order of nucleotides, also known as base calling.

Base calling accuracy can be measured a variety of different ways. In some embodiments base calling accuracy can be measured using a Q score (Phred quality score), which is a common metric to assess the accuracy of a sequencing run. Q scores are defined as logarithmically related to base calling error probability, where Q=−10 log P/log 10. In this system, if a base is assigned a Q score of 40, this is equal to the probability of an incorrect base call of 1 in 10,000 times, or 99.99% base calling accuracy; a lower Q score of 10 means, there is the probability of an incorrect call in 1 of 10 bases. Lower Q scores can lead to increases in false positive variant calls and reduces the overall confidence an investigator has in their sequencing data. Details of base calling and methods for calculating the quality of a base call are described in a variety of publications, including, e.g., Ledergerber et al. (Brief Bioinform. 2011 12: 489-497), Whiteford et al. (Bioinformatics 2009 25: 2194-2199), Erlich (Nat. Methods. 2008 5: 679-682) and Kao et al. (Genome Res. 2009 19: 1884-95), which are incorporated by reference for disclosure of those methods.

In some embodiments, the method may be used to identify positions that differ in the first and second repeats. In these embodiments, a position in the sequence read that is uncalled or associated with a low-quality score indicates that first and second repeat sequences differ at a nucleotide that corresponds to that position. By way of example, if the sequence of the first repeat is GATCGGATCGA (SEQ ID NO: 1) and the sequence of the second repeat is GATCG TATCGA (SEQ ID NO: 2), then the sequence read may contain only one copy of the sequence GATCGG[G/T] ATCGA (SEQ ID NO: 3), where "G/T" is a base that has a mixed signal and is therefore associated with a poor quality base call. In this example, the quality of the base calls for the non-G/T bases will be high and the quality of the base call for the G/T base will be poor because some of the signal for that position, as analyzed by the base celling algorithm, will be generated by extension of the first primer and some of the signal will be generated by the extension of the second primer, in the same reaction.

After a position that has a low-quality base call has been identified (or, in some cases a position that is uncalled), the method may further comprise analyzing the underlying signals for that position to determine the identities of the nucleotides at that position in the first and second repeats. For example, in the example described in the prior paragraph, the underlying signals (i.e., prior to base calling and referred to as primary sequence data) could be analyzed to determine that the position contains a mixture of G and T, thereby indicating that the first repeat contains a G or T at that position, and the second repeat contains the other nucleotide. As such, in any embodiment, the method may comprise reading a combination of signals obtained by simultaneous extension of the first and second primers to produce primary sequencing data, processing the primary sequencing data using a base-calling algorithm to produce a sequence read composed of a sequence of base calls, each base call associated with a quality score indicating the reliability of the base call; and outputting the sequence read based on the quality scores. The quality scores allow differences between the first and second repeats to be identified.

In some embodiments, the first and second sites in the template (i.e., the sequences to which the first and second primers bind) are the same sequence. In these embodiments, a single primer may be used in the method, where the primer binds to two sites in the template. In alternative embodiments, the first and second sites in the template (i.e., the sequences to which the first and second primers bind) may be different sequences. In these embodiments, two or more primers may be used in the method, where the primer binds different sequences in the template, one upstream of the first repeat and the other upstream from the second repeat.

Figure 3:
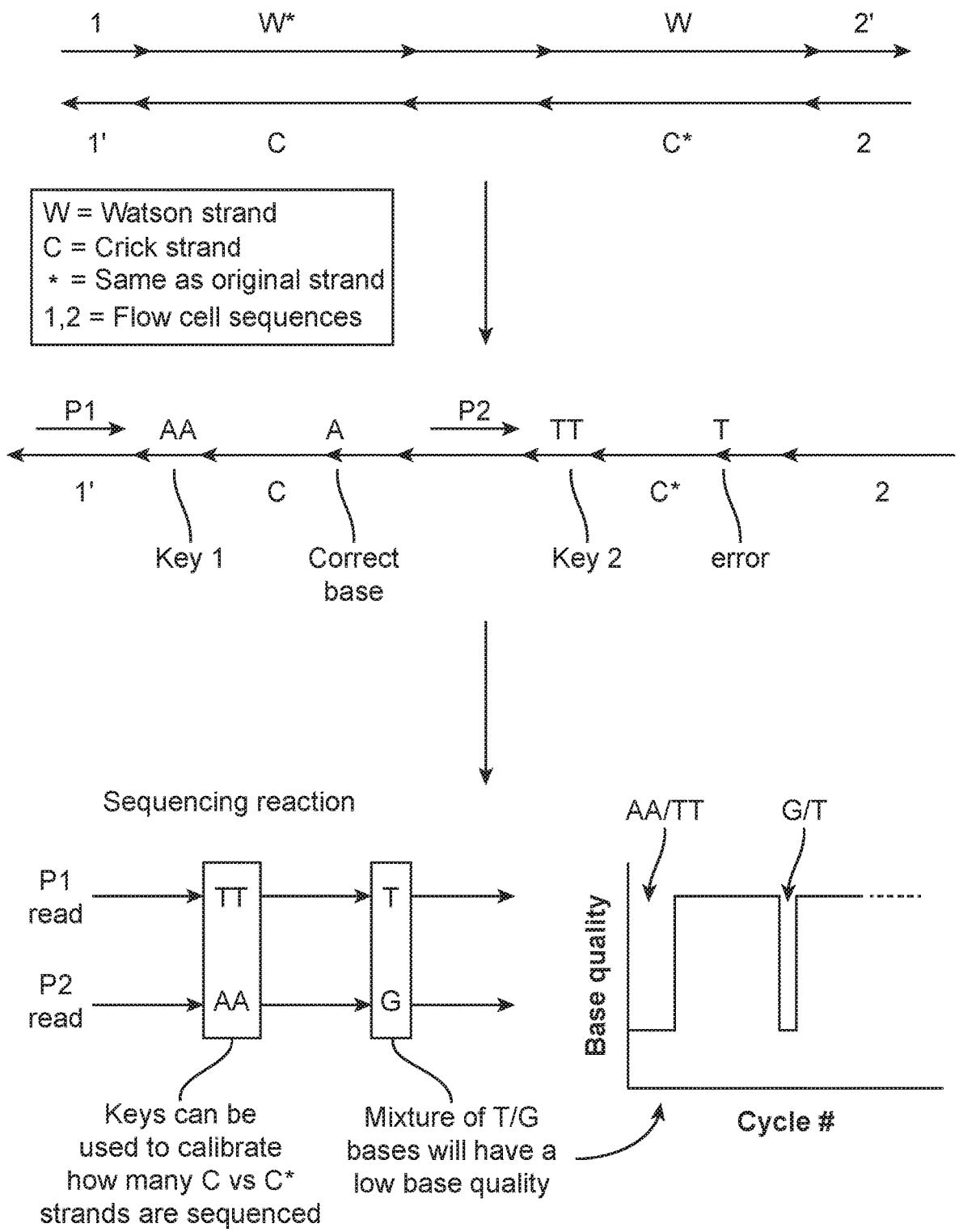
FIG. 3 schematically illustrates an example of the method.

In some embodiments, the method may involve determining how many strands of the first repeat are sequenced relative to the number of strands of the second repeat, or if a sufficient number of molecules have been sequenced. These embodiments may be implemented by adding a calibration sequence to the template, as shown in FIG. 3. In these embodiments, the template may comprise: a first calibrator sequence that is present between the first site and the first repeat; and a second calibrator sequence that is present between the second site and the second repeat, wherein the first and second calibrator sequences are the same length (e.g., may be two, three or four bases in length or the same number of flows in length, depending on the sequencing method used) and have a different sequence; and the sequence read of step (b) includes positions that correspond to the first and second calibrator sequences. In these embodiments, the underlying signals corresponding to the first and second calibrator sequences (prior to base calling) can be examined to determine how many strands of the first and second repeats are sequenced in the reaction. Likewise, the underlying signals corresponding to the first and second calibrator sequences (prior to base calling) can be examined to determine if a sufficient number of molecules have been sequenced.

In many sequencing-by-synthesis methods, template molecules are clonally amplified, and the amplification products are sequenced in a highly parallel fashion. Such methods are reviewed in, e.g., Metzker et al. (Genome Res. 2005 15:1767-1776) and Bentley (Curr. Opin. Genet. Dev. 2006 16: 545-55). In Illumina sequencing the templates are spread in a flow cell and immobilized on a support (typically glass; see Fedurco et al., Nucleic Acids Res. 2006 34:e22), where they are amplified in place by bridge PCR, which generates clusters of identical templates (or "colonies") on the support. As such, the present method may be implemented by amplifying the template on a substrate by bridge PCR to produce a colony that comprises copies of the template, hybridizing one or more primers to the colony, wherein a primer hybridizes to a first site that is upstream of the first repeat sequence and a primer hybridizes to a second site that is upstream of the second repeat sequence, wherein the first and second sites are: upstream of the first and second repeat sequences, respectively, equidistant from the first and second repeat sequences; and obtaining the sequence of the template by a sequencing-by-synthesis sequencing reaction to produce a sequence read that comprises a combination of the first and second repeat sequences. In some embodiments (and as illustrate in FIG. 3) the top and bottom strands of the bridge PCR amplification products may be sequenced by Illumina's sequencing method (which is referred to as "paired end" sequencing). As such, in some embodiments, the sequence of a top strand of a bridge PCR product can be compared to the sequence of a bottom strand of a bridge PCR product. Positions that are associated with a low-quality base call as a result of a difference in sequence between the first and second repeats should have a low-quality base call in both strands. In some embodiments, after sequencing both strands of the product by paired end sequencing one can produce a consensus sequence for the top strand of the initial double-stranded fragment and a consensus sequence for the bottom strand of the initial double-stranded fragment. Low quality bases can be masked or integrated into a model in which the quality scores are taken into account. Sequences that are not present in both the top and bottom strands of the initial double-stranded fragment can thereby be eliminated from future analysis.

FIG. 3 illustrates an example of the method. In this example, the template is a double stranded molecule and one or both strands need to be sequenced (sequencing of the bottom strand is shown). In this example, the direct repeat template has flow cell sequences (e.g., Illumina's P5 and P7 sequences) at the ends and a primer binding site between the first and second repeats. As shown, this molecule is amplified from a double-stranded fragment, where the first and second repeat sequences (W* and W or C* and C) are amplified from opposite strands of a double-stranded fragment of DNA and are identical except for positions that correspond to damaged nucleotides in the double-stranded fragment of DNA or errors that occur during amplification. As shown, the method may involve hybridizing two primers (designated $P_1$ and $P_2$, which can be the same or different) to the template (after it has been amplified). In this embodiment, the repeats each have a calibrator sequence (referred to as "key 1" and "key 2" that can be used to determine the relative number of copies of the first and second repeats that are sequenced in a reaction. As shown, the part of the sequence read obtained from primer $P_1$ should contain key 1 (TT) and the part of the sequence read obtained from primer $P_2$ should contain key 1 (AA). In this example, there is a difference in sequence in the first and second repeats, which can be identified as a base call with a low quality (as a result of the template have a mixed nucleotide at that position).

In embodiments in which there is non-informational sequence immediately downstream of a primer binding site, the primers may be extended but not read for the first few cycles, thereby allowing one to obtain the sequence of the keys and/or repeats faster.

In some embodiments, the direct repeat template may have different, non-complementary sequences (Sequences 1 and 2 in FIG. 3) in at least 10 nucleotides (e.g., at least 10, 12 or 14 nucleotides in length) that allow the fragments to be amplified by a single pair of primers: a first primer that hybridizes to one sequence and another that hybridizes to the complement of the other sequence. These sequences may be compatible with the sequencing platform being used. These sequences do not need to be at the very end of a molecule although, in many embodiments, the sequences are within 50 nt, e.g., within 30 nt of the end of molecule. As would be apparent, the template molecule should have a junction sequence between the first and second repeats. The junction sequence should be of 10 nucleotides (e.g., 10 to 100 nt). The template may contain a molecular barcode (e.g., a sample identifier or molecule identifier) at any position (outside of the repeats).

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood, e.g., from the blood of a patient or of a pregnant female. The DNA fragments used in the initial step of the method should be non-amplified DNA that has not been denatured beforehand.

The DNA in the initial sample may be made by extracting genomic DNA from a biological sample, and then fragmenting it. In some embodiments, the fragmenting may be done mechanically (e.g., by sonication, nebulization, or shearing, etc.) or using a double stranded DNA "dsDNA" fragmentase enzyme (New England Biolabs, Ipswich Mass.). In some of these methods (e.g., the mechanical and fragmentase methods), after the DNA is fragmented, the ends may be polished and A-tailed prior to ligation to one or more adaptors. Alternatively, the ends may be polished and ligated to adaptors in a blunt-end ligation reaction. In other embodiments, the DNA in the initial sample may already be fragmented (e.g., as is the case for FFPE (formalin-fixed paraffin embedded) samples and circulating cell-free DNA (cfDNA), e.g., ctDNA). The fragments in the initial sample may have a median size that is below 1 kb (e.g., in the range of 50 bp to 500 bp, or 80 bp to 400 bp), although fragments having a median size outside of this range may be used.

In some embodiments, the amount of DNA in a sample may be limiting. For example, the initial sample of fragmented DNA may contain less than 200 ng of fragmented human DNA, e.g., 1 pg to 20 pg, 10 pg to 200 ng, 100 pg to 200 ng, 1 ng to 200 ng or 5 ng to 50 ng, or less than 10,000 (e.g., less than 5,000, less than 1,000, less than 500, less than 100, less than 10 or less than 1) haploid genome equivalents, depending on the genome.

In some embodiments, sample identifiers (i.e., a sequence that identifies the sample to which the sequence is added, which can identify the patient, or a tissue, etc.) can be added to the polynucleotides prior to sequencing, so that multiple (e.g., at least 2, at least 4, at least 8, at least 16, at least 48, at least 96 or more) samples can be multiplexed. In these embodiments, the sample identifier may be ligated to the initial polynucleotides as part of the asymmetric adaptor, or the sample identifier may be ligated to the polynucleotides in the sub-samples, before or after amplification of those polynucleotides. Alternatively, the tag may be added by primer extension, i.e., using a primer that has a 3' end that hybridizes to an adaptor sequence, and a 5' tail that contains the sample identifier.

The population of direct repeat molecules may be made in a variety of different ways. These methods rely on creating circular molecules, retaining physical proximity between the two strands of one double-stranded DNA molecule, or physically isolating two strands of one double-stranded molecule, during manipulation steps. The methods also divide into strategies requiring one, or more, adaptor types. These methods can be done by fragmenting, polishing and then tailing the ends of the fragments before adaptor ligation. Alternatively, transposases can be used to add adaptor sequences. In some embodiments, standard transposons can be used but then modified to create a Y-shaped adaptor using oligonucleotide replacement (Grunenwald H, Baas B, Goryshin I, Zhang B, Adey A, Hu S, Shendure J, Caruccio N, Maffitt M 2011. Nextera PCR-free DNA library preparation for next-generation sequencing. [Poster presentation, AGBT 2011]; Gertz J, Varley K E, Davis N S, Baas B J, Goryshin I Y, Vaidyanathan R, Kuersten S, Myers R M 2012. Transposase mediated construction of RNA-seq libraries. Genome Res 22: 134-141).

In some embodiments, the direct repeat template may be made by (a) ligating adaptor sequences onto both ends of top and bottom strands of a population of fragments of double-stranded genomic DNA to produce double-stranded molecules comprising (i) a top strand comprising a 5' sequence (e.g., X) at the 5' end and a junction sequence (e.g., J) at the 3' end; and (ii) a bottom strand comprising a 5' sequence (e.g., Y') at the 5' end, and the complement of the junction sequence (J') at the 3' end; and (b) extending the 3' end of the top strands (i.e., the strand that contains sequence X) using the bottom strand as a template, thereby copying the complement of the bottom strand, as well as sequences J and Y, into the same molecule as the top strand to produce a direct repeat molecule of formula: X-TOP-J-BOT'-Y, wherein: (i) within each repeat molecule TOP and BOT' are amplified from opposite strands of a fragment of the double-stranded of genomic DNA and identical except for positions that correspond to damaged nucleotides in the double-stranded fragment of genomic DNA or amplification errors. In these embodiments, TOP and BOT' vary in the population and have a median length of at least 50 nucleotides and X and Y are different, non-complementary sequences of at least 10 nucleotides in length that do not vary in the population; and J is a junction sequence. Examples of this method are shown in the figures and described in greater detail below.

Figure 4:
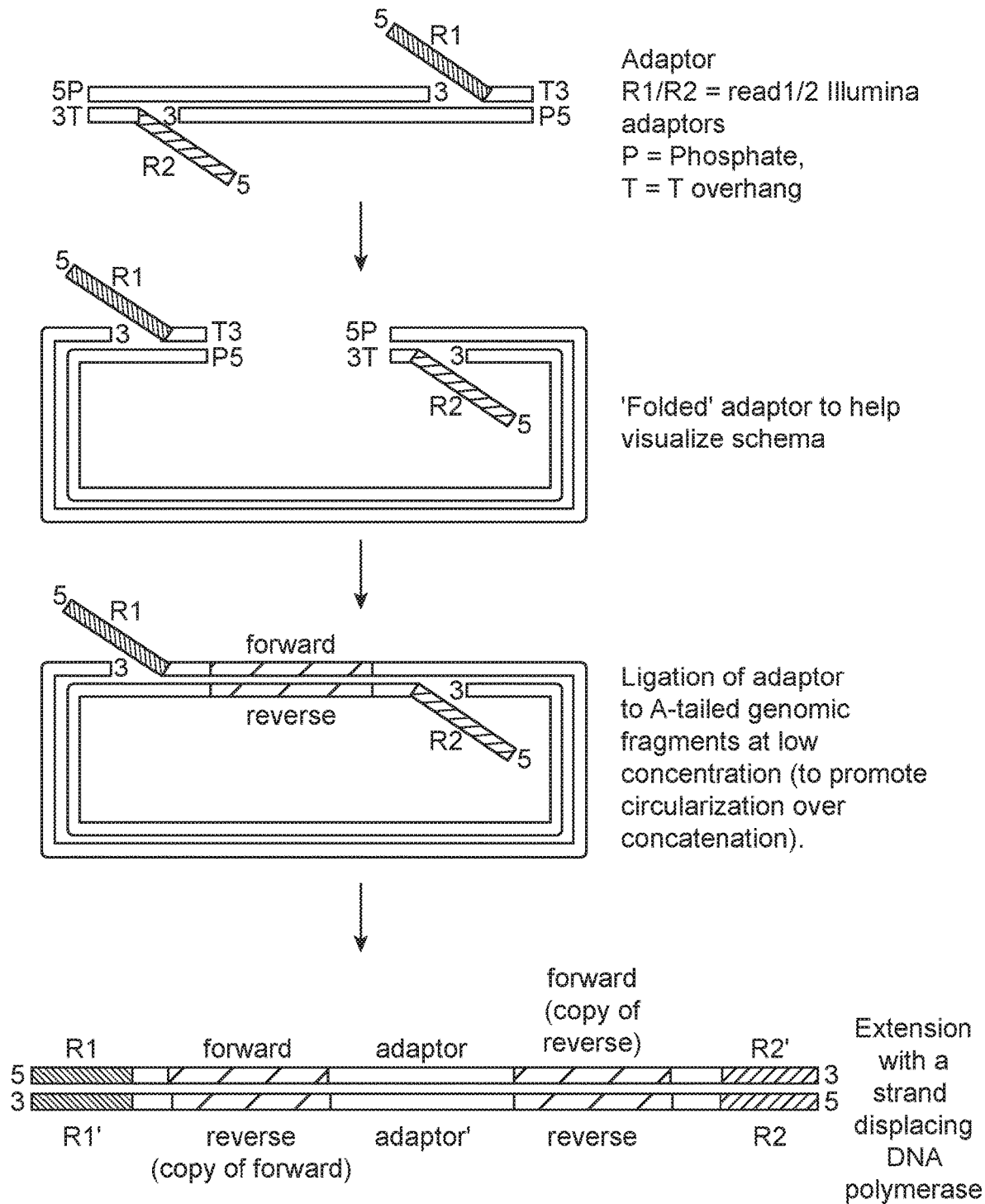
FIG. 4 schematically illustrates an exemplary method by which a direct repeat molecule can be produced.
Figure 5:
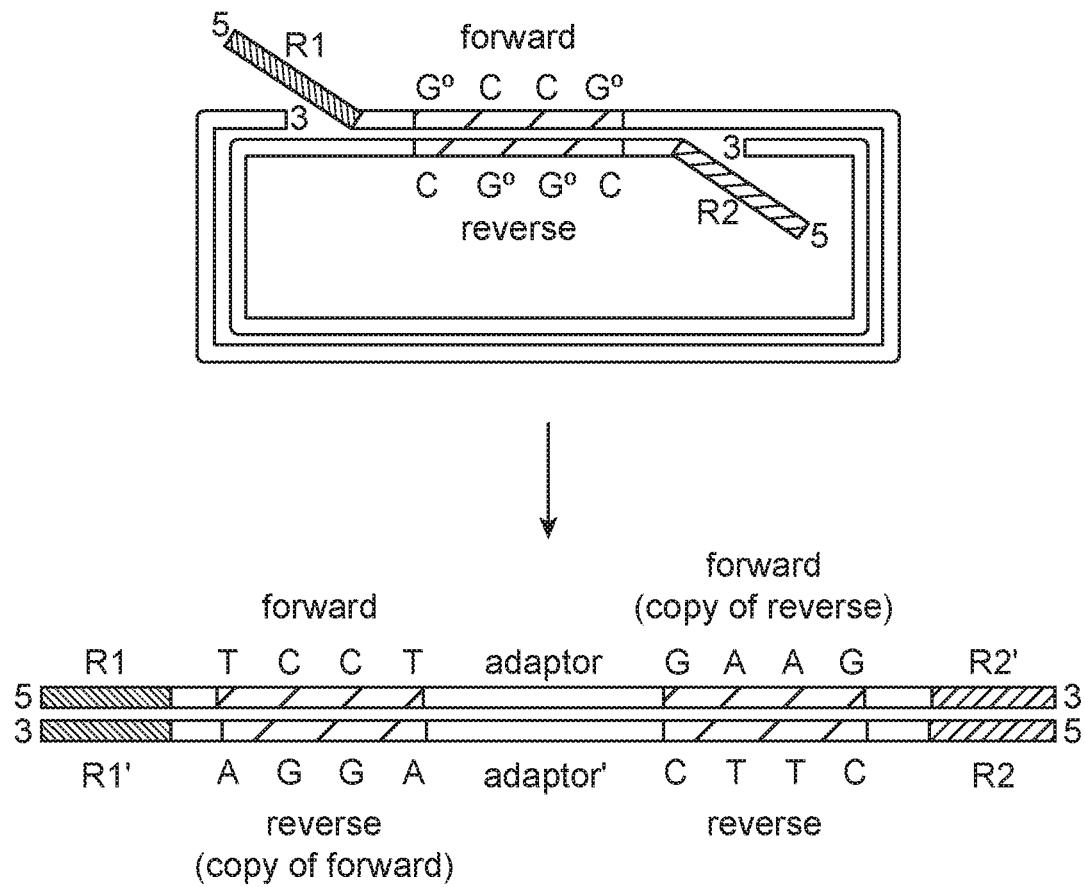
FIG. 5 schematically illustrates another exemplary method by which a direct repeat molecule can be produced.

In some embodiments and as shown in FIGS. 4 and 5, a direct repeat molecule may be made by ligating a single adaptor onto both ends of top and bottom strands of a population of fragments of double-stranded genomic DNA, such that, the individual molecules are in a covalently open circle and, in in the individual molecules in the population, sequence X is added onto the 5' end of the top strands of the fragment and sequence Y' is ligated onto the 5' of bottom strands of the fragments. This method involves extending the 3' end of the top strands (i.e., the strand that contains sequence X) using the bottom strand as a template, thereby copying the complement of the bottom strand, as well as sequence Y, into the same molecule as the top strand. Such a molecule can be amplified using primers that have a 3' end that is the same as or that hybridize to sequence X and Y. An example of such a method is illustrated in FIGS. 4 and 5, where the top strand of the fragments of genomic DNA are indicated as "forward" and "reverse" respectively and sequences X and Y' are indicated as sequences R1 and R2.

In some embodiments, the direct repeat molecules may be made by ligating a single adaptor onto both ends of top and bottom strands of a population of fragments of double-stranded genomic DNA, such that, the individual molecules are in a covalently closed circle and, in the individual molecules in the population, sequence X is added onto the 5' end of the top strands of the fragment and sequence Y' is ligated onto the 5' end of the bottom strands of the fragments. This method involves creating one or more nicks by reacting, e.g., an adaptor containing dUTP and a mixture of UDG/endonuclease IV, extending the 3' end of the top strands (i.e., the strand that contains sequence X) using the bottom strand as a template, thereby copying the complement of the bottom strand, as well as sequence Y, into the same molecule as the top strand. Such a molecule can be amplified using primers that have a 3' end that is the same as or that hybridizes to sequence X and Y.

A similar product may be made by emulsion PCR, using an immobilization approach, or rolling circle amplification, single adapter methods and greater than 1 adapter methods, as described in WO2018229547, which is incorporated by reference in its entirety. In some embodiments, the direct repeat template may be of the formula X-TOP-J-BOT'-Y, wherein (i) within each repeat molecule TOP and BOT' are amplified from opposite strands of a double-stranded fragment of genomic DNA and are identical except for positions that correspond to damaged nucleotides in the double-stranded fragment of genomic DNA or errors that occur during amplification; (ii) TOP and BOT' have a median length of at least 50 nucleotides; (iii) X and Y are different, non-complementary sequences of at least 10 nucleotides; and (iv) J is a junction sequence of, e.g., at least 10 nucleotides in length. In some embodiments, the direct repeat template may have a strand of the formula X-(T)TOP(A)-J-(T)BOT'(A)-Y, wherein (T) and (A) are thymine and adenine nucleotides that are immediately adjacent to TOP and BOT'. Such molecules may be made by, for example (a) ligating adaptor sequences onto both ends of top and bottom strands of a population of fragments of double-stranded genomic DNA to produce double-stranded molecules comprising: (i) a top strand comprising sequence X at the 5' end and sequence J at the 3' end; and (ii) a bottom strand comprising sequence Y' at the 5' end, and sequence J' at the 3' end; and (b) extending the 3' end of the top strands using the bottom strands as a template, thereby adding the complement of the bottom strands and sequence Y onto the end 3' end of the top strands. This method is illustrated in FIGS. 4 and 5.

Kits

Also provided by this disclosure is a kit for practicing the subject method, as described above. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

As would be readily apparent, the method described above may be employed to analyze any type of sample, including, but not limited to samples that contain heritable mutations, samples that contain somatic mutations, samples from mosaic individuals, pregnant females (in which some of the sample contains DNA from a developing fetus), and samples that contain a mixture of DNA from different sources. In certain embodiments, the method may be used identify a minority variant that, in some cases, may be due to a somatic mutation in a person.

In some embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medulloblastoma, polycythemia, lymphoma, sarcoma or multiple myeloma (see, e.g., Chial 2008 Proto-oncogenes to oncogenes to cancer. Nature Education 1:1). Other oncogenic mutations (which may be somatic mutations) of interest include mutations in, e.g., APC, AXIN2, CDH1, GPC3, CYLD, EXT1, EXT2, PTCH, SUFU, FH, SDHB, SDHC, SDHD, VHL, TP53, WT1, STK11/LKB1, PTEN, TSC1, TSC2, CDKN2A, CDK4, RB1, NF1, BMPR1A, MEN1, SMAD4, BHD, HRPT2, NF2, MUTYH, ATM, BLM, BRCA1, BRCA2, FANCA, FANCC, FANCD2, FANCE, FANCF, FANCG, NBS1, RECQL4, WRN, MSH2, MLH1, MSH6, PMS2, XPA, XPC, ERCC2-5, DDB2 or MET, which may be associated with colon, thyroid, parathyroid, pituitary, islet cell, stomach, intestinal, embryonal, bone, renal, breast, brain, ovarian, pancreatic, uterine, eye, hair follicle, blood or uterus cancers, pilotrichomas, medulloblastomas, leiomyomas, paragangliomas, pheochromocytomas, hamartomas, gliomas, fibromas, neuromas, lymphomas or melanomas. In some embodiments, the method may be employed to detect a somatic mutation in genes that are implicated in cancer, e.g., CTNNB1, BCL2, TNFRSF6/FAS, BAX, FBXW7/CDC4, GLI, HPVE6, MDM2, NOTCH1, AKT2, FOXO1A, FOXO3A, CCND1, HPVE7, TAL1, TFE3, ABL1, ALK, EPHB2, FES, FGFR2, FLT3, FLT4, KRAS2, NTRK1, NTRK3, PDGFB, PDGFRB, EWSR1, RUNX1, SMAD2, TGFBR1, TGFBR2, BCL6, EVI1, HMGA2, HOXA9, HOXA11, HOXA13, HOXC13, HOXD11, HOXD13, HOX11, HOX11L2, MAP2K4, MLL, MYC, MYCN, MYCL1, PTNP1, PTNP11, RARA, SS18 (see, e.g., Vogelstein and Kinzler 2004 Cancer genes and the pathways they control. Nature Medicine 10:789-799). The method of embodiment may be employed to detect any somatic mutation that is implicated in cancer which is catalogued by COSMIC (Catalogue of Somatic Mutations in Cancer), data of which can be accessed on the internet.

Other mutations of interest include mutations in, e.g., ARID1A, ARID1B, SMARCA4, SMARCB1, SMARCE1, AKT1, ACTB/ACTG1, CHD7, ANKRD11, SETBP1, MLL2, ASXL1, which may be at least associated with rare syndromes such as Coffin-Siris syndrome, Proteus syndrome, Baraitser-Winter syndrome, CHARGE syndrome, KBG syndrome, Schinzel-Giedion syndrome, Kabuki syndrome or Bohring-Opitz syndrome (see, e.g., Veltman and Brunner 2012 De novo mutations in human genetic disease. Nature Reviews Genetics 13:565-575). Hence, the method may be employed to detect a mutation in those genes.

In other embodiments, the method may be employed to detect a mutation in genes that are implicated in a variety of neurodevelopmental disorders, e.g., KAT6B, THRA, EZH2, SRCAP, CSF1R, TRPV3, DNMT1, EFTUD2, SMAD4, LIST, DCX, which may be associated with Ohdo syndrome, hypothyroidism, Genitopatellar syndrome, Weaver syndrome, Floating-Harbor syndrome, hereditary diffuse leukoencephalopathy with spheroids, Olmsted syndrome, ADCA-DN (autosomal-dominant cerebellar ataxia, deafness and narcolepsy), mandibulofacial dysostosis with microcephaly or Myhre syndrome (see, e.g., Ku et al. (2012) A new paradigm emerges from study of de novo mutations in the context of neurodevelopmental disease. Molecular Psychiatry 18:141-153). The method may also be employed to detect a somatic mutation in genes that are implicated in a variety of neurological and neurodegenerative disorders, e.g., SCN1A, MECP2, IKBKG/NEMO or PRNP (see, e.g., Poduri et al. (2014) Somatic mutation, genetic variation, and neurological disease. Science 341(6141):1237758).

In some embodiments, a sample may be collected from a patient at a first location, e.g., in a clinical setting such as in a hospital or at a doctor's office, and the sample may be forwarded to a second location, e.g., a laboratory where it is processed, and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

The method may be used to analyze diseases that are associated with mutations, transplant rejection and has applications in non-invasive prenatal testing.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of sequencing comprising:
   (a) obtaining a template that comprises a single copy of a first repeat sequence and a single copy of a second repeat sequence, wherein the first and second repeat sequences are in a direct repeat and either identical or nearly identical;
   (b) in the same reaction, hybridizing a primer to a first site that is upstream of the first repeat sequence and hybridizing a primer to a second site that is upstream of the second repeat sequence, wherein the first and second sites are:
      (i) upstream of the first and second repeat sequences, respectively, and
      (ii) equidistant from the first and second repeat sequences; and
   (c) subjecting the hybridization product of (b) to a sequencing-by-synthesis sequencing reaction to produce a sequence read that comprises a combination of the first and second repeat sequences;
   wherein the template of (a) is produced by amplifying a double-stranded fragment of DNA, wherein the first and second repeat sequences are amplified from opposite strands of a double-stranded fragment of DNA, respectively, and are identical except for positions that correspond to damaged nucleotides in the double-stranded fragment of DNA or errors that occur during amplification.

2. The method of claim 1, wherein the double-stranded fragment of DNA is genomic DNA.

3. The method of claim 2, wherein the genomic DNA is eukaryotic genomic DNA.

4. The method of claim 2, wherein the genomic DNA is isolated from a tissue biopsy.

5. The method of claim 2, wherein the genomic DNA is cell-free DNA (cfDNA).

6. The method of claim 2, wherein the genomic DNA is microbial genomic DNA.

7. The method of claim 2, wherein the genomic DNA is viral genomic DNA.

8. The method of claim 1, wherein the sequence read of (c) comprises, for each position of the sequence read, a quality score indicating the reliability of the base(s) called at that position.

9. The method of claim 8, wherein a position in the sequence read that is uncalled or associated with a low-quality score indicates that first and second repeat sequences differ at a nucleotide that corresponds to that position.

10. The method of claim 9, further comprising analyzing primary sequencing data for a position that has a low-quality score to determine the identities of the nucleotides at that position in the first and second repeats.

11. The method of claim 1, wherein step (c) comprises:
    (i) reading a combination of signals obtained by simultaneous extension of the first and second primers to produce primary sequencing data;
    (ii) processing the primary sequencing data using a base-calling algorithm to produce a sequence read composed of a sequence of base calls, each base call associated with a quality score indicating the reliability of the base call; and
    (iii) outputting the sequence read based on (ii).

12. The method of claim 1, wherein the sequencing-by-synthesis of step (c) comprises simultaneously extending the first and second primers in the presence of reversible chain terminators.

13. The method of claim 1, wherein the first and second sites in the template are the same sequence.

14. The method of claim 1, wherein the first and second sites in the template are different sequences.

15. The method of claim 1, wherein the template comprises:
    (i) a first calibrator sequence that is present between the first site and the first repeat; and
    (ii) a second calibrator sequence that is present between the second site and the second repeat, wherein the first and second calibrator sequences are the same length and have a different sequence; and the sequence read of step (c) includes positions that correspond to the first and second calibrator sequences.

16. The method of claim 15, further comprising analyzing the signals corresponding to the first and second calibrator sequences to determine how many strands of the first and second repeats are sequenced in the reaction.

17. The method of claim 1, wherein first and second repeats are less than 2,000 nucleotides in length.

18. The method of claim 1, wherein the method is done by:

amplifying the template on a substrate by bridge PCR to produce a colony that comprises copies of the template;

hybridizing one or more primers to the colony, wherein a primer hybridizes to a first site that is upstream of the first repeat sequence and a primer hybridizes to a second site that is upstream of the second repeat sequence, wherein the first and second sites are: upstream of the first and second repeat sequences, respectively, and equidistant from the first and second repeat sequences; and obtaining the sequence of the template by a sequencing-by-synthesis sequencing reaction to produce a sequence read that comprises a combination of the first and second repeat sequences.

19. The method of claim 11, further comprising:

identifying a base in the sequence read as being associated with an unreliable base call;

determining the identified base as being associated with signals corresponds to two different bases; and indicating that the base corresponds to a damaged nucleotide or an error that occurred during amplification.

* * * * *

SEQUENCE LISTING

<160> NUMBER OF SEQ ID NOS: 3

<210> SEQ ID NO 1
<211> LENGTH: 11
<212> TYPE: DNA
<213> ORGANISM: artificial sequence
<220> FEATURE:
<223> OTHER INFORMATION: synthetic oligonucleotide

<400> SEQUENCE: 1

```
gatcggatcg a                                                                11

<210> SEQ ID NO 2
<211> LENGTH: 11
<212> TYPE: DNA
<213> ORGANISM: artificial sequence
<220> FEATURE:
<223> OTHER INFORMATION: sythetic oligonucleotide

<400> SEQUENCE: 2
gatcgtatcg a                                                                11

<210> SEQ ID NO 3
<211> LENGTH: 12
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: n at position 7 is a G or T

<400> SEQUENCE: 3
gatcggnatc ga                                                               12
```